US00PP31128P2

(12) United States Plant Patent
Ault

(10) Patent No.: US PP31,128 P2
(45) Date of Patent: Nov. 26, 2019

(54) ***EUPATORIUM* PLANT NAMED 'SUMMER SNOW'**

(50) Latin Name: *Eupatorium maculatum*
Varietal Denomination: Summer Snow

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 0 days.

(21) Appl. No.: 16/350,412

(22) Filed: Nov. 13, 2018

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Eupatorium*, 'Summer Snow', characterized by its florets that are white in color, stems that are green in color, compact plant habit, its early blooming habit, its florets that produce a light vanilla-like fragrance, its wide soil adaptability; from very wet to dry soils, and its excellent resistance to powdery mildew.

2 Drawing Sheets

Botanical classification: *Eupatorium maculatum.*
Variety denomination: 'Summer Snow'.

BACKGROUND OF THE INVENTION

The present invention relates to a new and distinct cultivar of *Eupatorium maculatum* and will be referred to hereafter by its cultivar name, 'Summer Snow'. 'Summer Snow' is a new herbaceous perennial suitable for landscape plantings.

The new cultivar is the result of a controlled breeding program conducted by the Inventor in Glencoe, Ill. The intent of the program is to develop new cultivars of *Eupatorium* that are compact, have white flowers and an earlier blooming season. The new cultivar arose from self-pollination of unknown *Eupatorium maculatum* in July of 2011. 'Summer Snow' was selected as a single unique plant from the resulting seedlings in October of 2012.

The new cultivar was first asexually propagated by shoot tip cuttings and division by the Inventor in Glencoe, Ill. in June of 2013. Asexual propagation has determined that the characteristics of this cultivar are stable and are reproduced true to type in successive generations.

SUMMARY OF THE INVENTION

The following traits have been repeatedly observed and represent the characteristics of the new *Eupatorium*. These attributes in combination distinguish 'Summer Snow' as a unique cultivar of *Eupatorium.*

1. 'Summer Snow' exhibits florets that are white in color.
2. 'Summer Snow' exhibits stems that are green in color.
3. 'Summer Snow' exhibits a compact plant habit.
4. 'Summer Snow' exhibits an early blooming habit.
5. 'Summer Snow' exhibits florets that produce a light vanilla-like fragrance.
6. 'Summer Snow' exhibits wide soil adaptability; from very wet to dry soils.

7. 'Summer Snow' exhibits excellent resistance to powdery mildew.

The new cultivar of *Eupatorium* can be readily distinguished from other cultivars of *Eupatorium* known to the Inventor. The seed parent of 'Summer Snow' differs from 'Summer Snow' in having larger leaves, a later blooming period, and a taller plant height. 'Summer Snow' can be most closely compared to *Eupatorium maculatum* 'Snowball' (U.S. Plant Pat. No. 22,869) and *Eupatorium fistulosum* 'Ivory Tower' (not patented). Both cultivars are similar to 'Summer Snow' in having florets that are white in color and similar plant height. 'Snowball' differs from 'Summer Snow' in having a later blooming period, produces no flower fragrance and stems that are glabrous with no pubescence. 'Ivory Tower' differs from 'Summer Snow' in having a later blooming period, poor resistance to powdery mildew, stems that are hollow and stems that are glabrous with no pubescence.

BRIEF DESCRIPTION OF THE DRAWINGS

The accompanying colored photographs illustrate the overall appearance and distinct characteristics of a 3-year-old plant of the new *Eupatorium* as grown outdoors in a trial plot in Glencoe, Ill.

Figure 1:
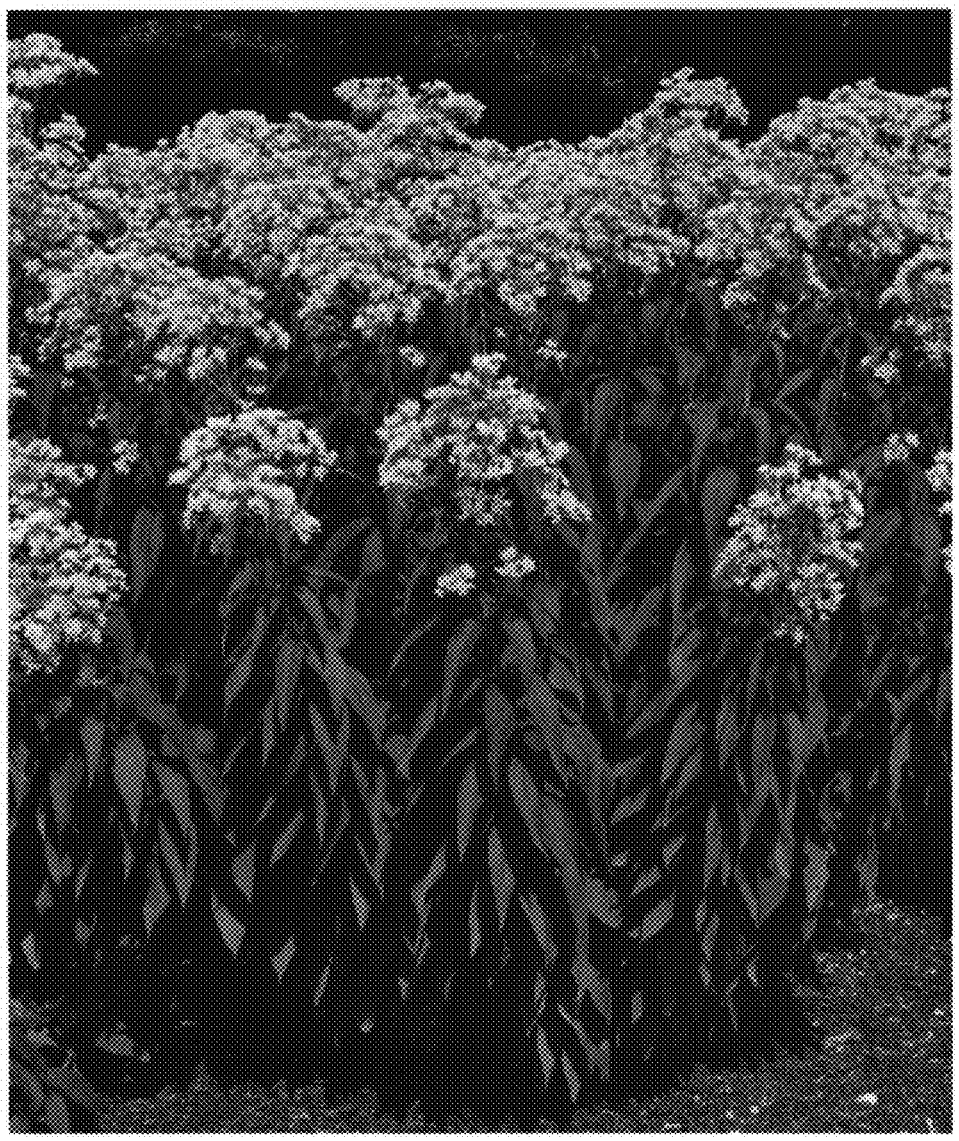
FIG. 1 was taken in July and provides a view of the plant habit of 'Summer Snow' in bloom.
Figure 2:
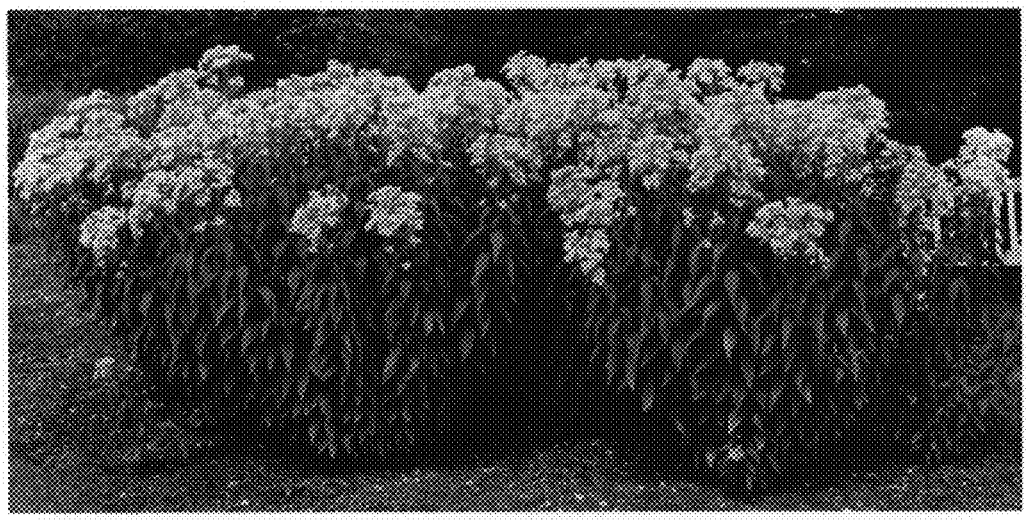
FIG. 2 was taken in July and provides a side view of 2 plants of 'Summer Snow'.
Figure 3:
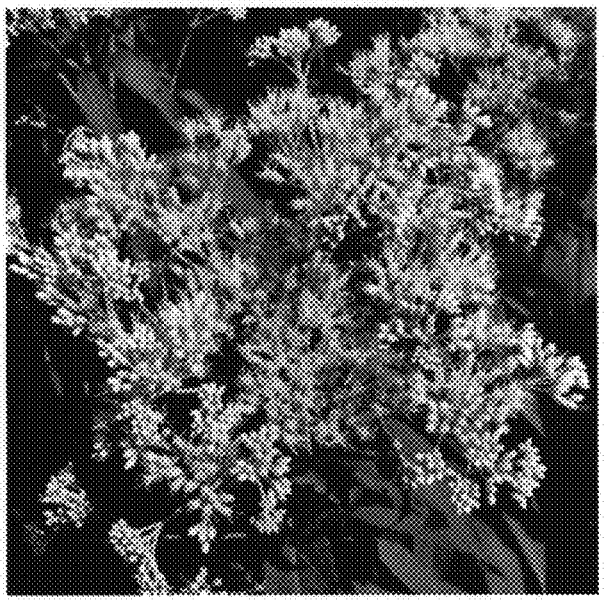
FIG. 3 was taken in July and provides a close-up view of the inflorescences of 'Summer Snow'.

The colors in the photographs are as close as possible with digital photography techniques available, the color values cited in the detailed botanical description accurately describe the colors of the new *Eupatorium.*

DETAILED BOTANICAL DESCRIPTION

The following is a description of one year old plants of the new cultivar as grown outdoors in 2-quart containers. The description of the plant habit and mature height and spread were observed on 3 to 5 year-old plants of the new cultivar as grown in a trial bed in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season.*—5 to 6 weeks from early July through mid to late August in northern Illinois.

*Plant habit.*—Herbaceous perennial with tall upright stems.

*Height and spread.*—A 2 year-old plant reaches 120 cm in height, 80 cm in width, a 3 year-old plant reaches 160 cm in height and 150 cm in width.

*Hardiness.*—At least in U.S.D.A. Zones 4 to 7.

*Diseases resistance.*—Excellent resistance to powdery mildew when grown in comparison trials with other cultivars of *Eupatorium.*

*Root description.*—Fibrous.

*Propagation.*—Shoot tip cuttings and division.

*Growth rate.*—Vigorous.

Stem description:

*Stem color.*—146C with spots of 137C.

*Stem surface.*—Ridged with short stuff hairs (rough to touch).

*Stem size.*—About 41 cm in length (to base of primary peduncle) and 9 mm in width.

*Branching habit.*—Basal branches.

*Internode length.*—Average of 3.5 cm.

Foliage description:

*Leaf division.*—Simple.

*Leaf shape.*—Lanceolate-elliptic.

*Leaf base.*—Cuneate.

*Leaf apex.*—Acuminate.

*Leaf margin.*—Serrate.

*Leaf venation.*—Pinnate, only conspicuous on lower surface, color upper and lower surface 146D.

*Leaf attachment.*—Petiolate.

*Leaf arrangement.*—Variable, primarily whorls or alternate.

*Leaf number.*—Average of 11 per stem portion 22 cm in length.

*Leaf surface.*—Dull and glabrous on upper and lower surface.

*Leaf color.*—Young and mature upper surface N137A, young and mature a lower surface; 147B.

*Leaf size (fully expanded).*—Average of 19 cm in length and 6 cm in width when mature.

*Leaf fragrance.*—None.

Inflorescence description:

*Inflorescence type.*—Cymose panicle of composite inflorescences comprised of disk florets only.

*Inflorescence size.*—Cymose panicle; an average of 30 cm in height and 20 cm in width, composite; an average of 1 cm in length and 5 mm in width.

*Inflorescence number.*—1 panicle per stem, an average of 16 cymes per panicle, an average of 100 composite inflorescences per cyme.

*Peduncles.*—Round in shape, primary peduncle is an average of 15 cm in length and 4 mm in width, secondary peduncles (on cymes) are an average of 8 cm in length and 3 mm in width, tertiary peduncles are an average of 4 cm in length and 32 mm in width, peduncles of composites is an average of 3 mm in length and 1 mm in width, 144D in color with primary peduncle having spots of 137B, surface is pubescent, average internode length for secondary peduncles is 6 cm, peduncle leaves on primary and secondary peduncles (an average of 14 per panicle) are up to 8.5 cm in length and 1.7 mm in width on petioles up to 7 mm in length and 1.5 mm in width (all other leaf and petiole characteristics match stem leaf).

*Pedicels.*—None.

*Inflorescence buds.*—Oblong in shape, 7 mm in length in depth and 2.5 mm in diameter, color 155C with bracts at very base 138A, surface in imbricate due to bracts.

*Flower fragrance.*—Very slight, vanilla-like.

*Persistence of flowers.*—Persistent.

*Lastingness of inflorescence.*—About 3 weeks.

Involucral bracts:

*Bract number.*—Average of 12.

*Bract arrangement.*—Imbricate.

*Bract size.*—An average of 34 mm in length and 1.5 mm in width.

*Bract color.*—155C and suffused with 137C on both surfaces.

*Bract texture.*—Both surfaces glabrous and shiny.

*Bract apex.*—Acute.

*Bract base.*—Cuneate to attenuate.

*Bract margins.*—Entire.

*Bract shape.*—Lanceolate to linear.

Disk flowers (perfect):

*Number.*—About 12.

*Shape.*—Tubular, corolla is fused.

*Size.*—About 8 mm in length and 1 mm in width.

*Color.*—155B and suffused slightly near base with 144C.

*Receptacle.*—Conical, about 2 mm in height and width, 137C in color.

*Phyllaries.*—Numerous, very fine, an average of 6 mm in length, 155C in color with base 144C.

Reproductive organs:

*Pistils.*—1, stigma; linear, about 2 mm in length and <1 mm in diameter, 155B in color, style; about 8 mm in length, 155B in color, ovary superior; <1 mm in width and 2 mm in length, lanceolate in shape, 144C in color.

*Stamens.*—About 4, filaments; 5 mm in length, 155B in color, anthers; 1.5 mm in length, about 200B in color, pollen; none observed.

*Fruit and seed.*—Not observed to date.

It is claimed:

1. A new and distinct cultivar of *Eupatorium* plant named 'Summer Snow' as described and illustrated herein.

* * * * *